United States Patent [19]
Clinton

[11] 4,334,527
[45] Jun. 15, 1982

[54] SUPPORT APPARATUS FOR PROSTHETIC APPLIANCE

[76] Inventor: Robert E. Clinton, 6403 S. 5th Ave., Phoenix, Ariz. 85041

[21] Appl. No.: 223,253

[22] Filed: Jan. 8, 1981

[51] Int. Cl.³ .............................................. A61F 5/00
[52] U.S. Cl. ................................................. 128/79
[58] Field of Search .................... 128/79, 1 R, 98, 99, 128/111, 125, 138

[56] References Cited

U.S. PATENT DOCUMENTS

| | | | |
|---|---|---|---|
| 3,554,184 | 1/1971 | Habib | 128/98 |
| 4,022,196 | 5/1977 | Clinton | 128/79 |

FOREIGN PATENT DOCUMENTS 2460812  7/1976  Fed. Rep. of Germany ........ 128/79

Primary Examiner—Dalton L. Truluck
Attorney, Agent, or Firm—H. Gordon Shields

[57] ABSTRACT

Support apparatus for a prosthetic appliance includes a generally wide, U-shaped element with two ends, one end for pivotally attaching the support apparatus to the prosthetic appliance and the opposite end adapted to be disposed against a user's back, with the intermediate portion of the base member comprising a curved portion adapted to extend through the crotch of the user and to be fastened at the back to a belt which is also fastened to the prosthetic appliance.

10 Claims, 3 Drawing Figures

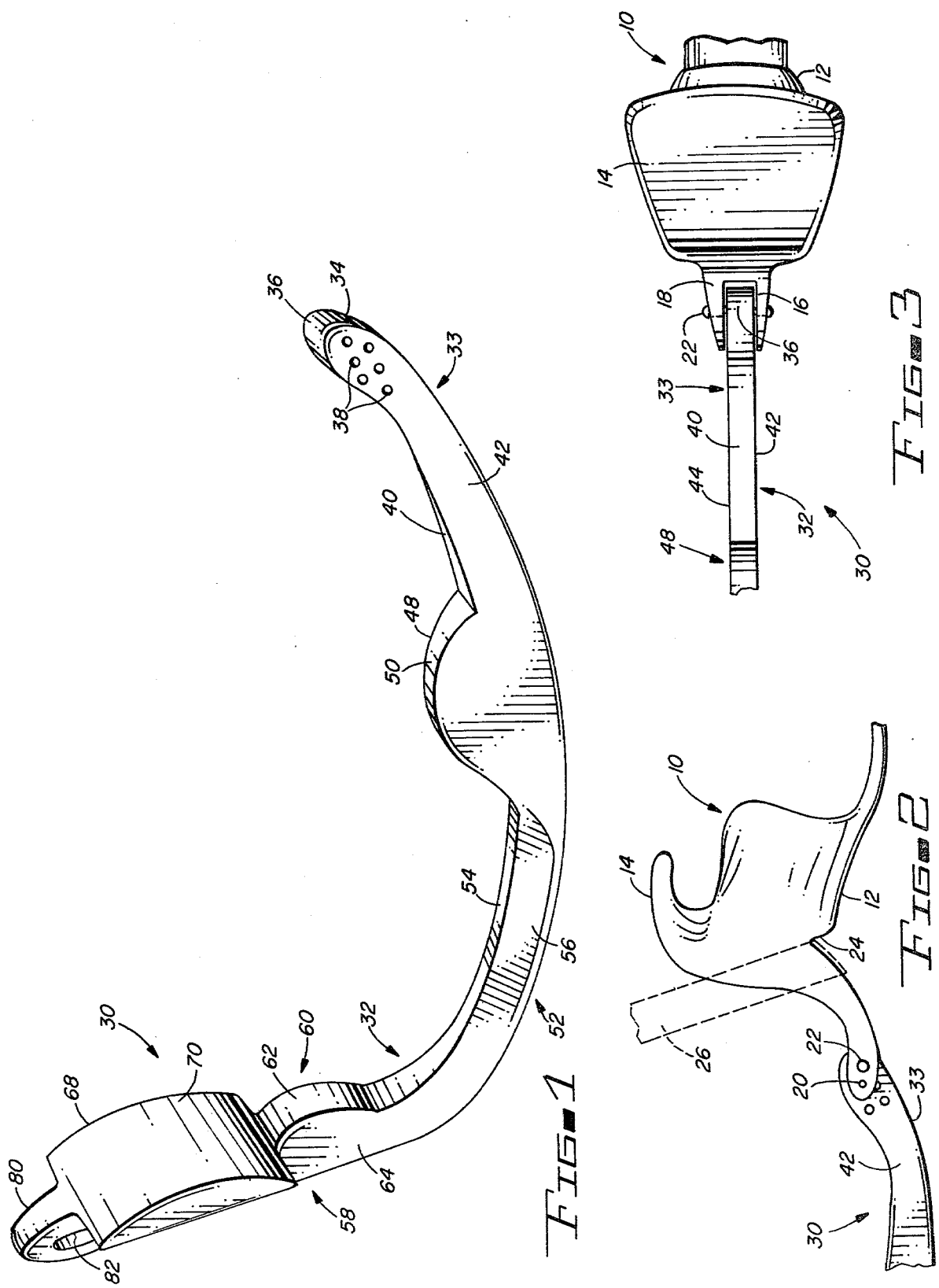

SUPPORT APPARATUS FOR PROSTHETIC APPLIANCE

BACKGROUND OF THE INVENTION

1. Field of the Invention

This invention relates to a support for a prosthetic appliance, and, more particularly, to a support element adapted to be secured to a prosthetic penile apparatus for supporting the prosthetic apparatus and for securing the apparatus to the user's torso when used in conjunction with a belt.

2. Description of the Prior Art

A penile prosthetic apparatus, usable with the apparatus of the present invention, is generally described in U.S. Pat. No. 4,022,196, to the inventor hereof. The apparatus described in the '196 patent is illustrated as being secured to the torso of a user by means of a belt. The use of the belt has shortcomings which are overcome by the apparatus of the present invention.

The apparatus of the present invention comprises a relatively rigid support structure for securing a prosthetic appliance, such as disclosed in the '196 patent, to the torso of the user, while allowing a pivoting attachment between the prosthetic appliance and the support element in combination with a belt which extends around the torso of the user and fastens to both the support member and to the prosthetic appliance.

The prior art support elements comprise generally belts, such as illustrated in the '196 patent. The belts, being relatively flexible, provide a two-point attachment between the prosthetic appliance and the user. The two-point suspension comprises opposite sides of the prosthetic appliance, with the belt then extending around the torso of the user. The belt support, by itself, does not provide a sufficiently rigid connection between the user and the prosthetic appliance to allow the prosthetic appliance to be used to the best advantage of the user thereof and his partner. That is, there may be movement of the user that is not translated into a direct movement of the appliance, due to lack of a relatively rigid connection between the user and the appliance. However, with the relatively rigid or inflexible support element disclosed herein, which comprises a third suspension point between the user and the prosthetic appliance, the problems of the prior art are overcome.

SUMMARY OF THE INVENTION

The apparatus disclosed and claimed herein comprises a relatively inflexible support element having a generally wide or elongated U-shaped configuration adapted to be secured at one end by a pivoting engagement to a penile prosthetic appliance and at its opposite end to be secured to a belt which is in turn also secured to the prosthetic appliance and which extends about the user's torso. The connection between the belt and the support apparatus is at the back of the user, with the elongated U-shaped support member extending through the crotch of the user and positioned by a pair of positioning protuberances on the apparatus to fit the anatomy of the male user.

Among the objects of the present invention are the following:

To provide new and useful support apparatus for a penile prosthetic appliance;

To provide new and useful support apparatus for securing a prosthetic appliance to a user of the appliance;

To provide new and useful support apparatus having a relatively wide, U-shaped configuration adapted to be secured to a user of a prosthetic appliance;

To provide new and useful support apparatus for a prosthetic penile appliance to secure the appliance to a user for coordinated and direct movement of the appliance relative to corresponding movement of the user; and To provide new and useful support apparatus for a prosthetic penile apparatus adapted for a pivoting engagement with the prosthetic appliance and extending through the crotch of a user to the user's back.

BRIEF DESCRIPTION OF THE DRAWING

FIG. 1 is a perspective view of the apparatus of the present invention.

FIG. 2 is a side view of a portion of the apparatus of FIG. 1, illustrating its connection to a prosthetic appliance for use of the apparatus.

FIG. 3 is a top view of the apparatus of FIG. 2.

DESCRIPTION OF THE PREFERRED EMBODIMENT

FIG. 1 comprises a perspective view of prosthetic support apparatus 30 of the present invention. FIGS. 2 and 3 illustrate the connection of the prosthetic support apparatus 30 to a prosthetic penile apparatus 10. FIG. 2 is a side view, while FIG. 3 is a top view, both of which illustrate the attachment of the support apparatus 30 to the prosthesis 10, which comprises the use environment for the support apparatus 30. FIGS. 1, 2, and 3 will be referred to in the following discussion.

The prosthesis 10 comprises a prosthetic penile apparatus having a base 12, with two appendages to the base 12. An upper plate 14 extends upwardly and forwardly from the base 12, and a yoke, comprising a pair of yoke arms 16 and 18, extends downwardly and rearwardly from the base 12. The yoke, consisting of the two yoke arms 16 and 18, defines an attachment or securement point for the support apparatus 30. The yoke arms are generally parallel to each other and each arm includes a plurality of aligned apertures 20. The apertures 20 are used to secure the support 30 to the base 12 of the prosthesis 10 by means of a pin 22 which extends through the aligned apertures in the yoke arms and through the support 30.

At the juncture of the base 12 and the yoke arms there is a notch 24. A strap 26 is shown in phantom in FIG. 2 as being disposed in the notch 24 and extending upwardly. The strap 26 encircles the torso of the user of the prosthetic apparatus 10 and is used in conjunction with the support 30 to secure the prosthetic appliance 10 to the user's body.

The support apparatus 30 includes a curved base 32 which generally includes three portions or sections, a front portion 33, an intermediate portion 52, and a back or rear portion 58. The base 32 is curved, almost continuously, from a forward tip 36 to a back or rear tip 80. However, the curvature is not symmetrical. The curvature of the front portion 33 and the intermediate portion 52 is relatively constant and continuous, but the rear portion 58 has an increased curvature with respect to the front and intermediate portions.

The base 32 includes a generally flat bottom surface 34 which extends from the forward or front tip 32 to the rear tip 80. Extending through the forward tip 36 is a plurality of apertures 38. For adjusting the support 30 to the prosthesis 10, to accommodate a single support 30 to individuals of various sizes, an appropriate aperture 38 of the support 30 is aligned with a pair of the apertures 20 in the yoke arms of the prosthesis 10, and a pivoting connection is made between the prosthesis 10 and the base 30 by means of the pin 22.

With the pin 22 securing the support 30 and the prosthesis 10 together, the prosthesis 10 may pivot with respect to the support 30, but movement of the support 30 also results in a corresponding movement of the prosthesis 10. The belt 26 further supports the prosthesis 10 and aids in positioning the prosthesis 10, and in holding the prosthesis 10 in the desired position relative to the base 30, but yet allows the prosthesis 10 to move, with a natural movement, according to movement of the torso of the user. Since the connection between the support 30 and the prosthesis 10 is relatively rigid, and since the support 30 and the prosthesis 10 are both secured to the user's torso, movements of the user are transmitted to the prosthesis for direct and corresponding movement.

The base 32 includes a front upper or top surface 40 which extends from the front tip 36 to the rear tip 80. The front or top surface 40 varies in width, and follows the irregular contour of the base 32, as will be discussed in detail below.

The base 32 also includes a pair of sides 42 and 44 which extend between the bottom surface 34 and the top surface 40. As best seen in FIG. 3, the sides 42 and 44 are generally parallel to each other in the front or forward portion 33 of the base 32.

A forward positioning protuberance or hump 48 extends upwardly from the base 32 and comprises the rear section of the front portion 33. The protuberance 48 includes a generally convex top surface 50. The intermediate portion 52 of the base 32 extends rearwardly from the positioning protuberance 48. The top surface 50 of the protuberance 46 is a continuation of the upper or top surface 40.

The intermediate portion 52 extends from the positioning protuberance 48 to a rear positioning protuberance 60. The rear positioning protuberance 60 is also generally convex in configuration. However, it is not as large as is the front positioning protuberance 48. The protuberance 60 includes a convex top or outer surface 62.

The configuration of the intermediate portion 52 is somewhat different in cross section from the configuration of the forward portion 33. While the bottom surface 34 is generally continuous and flat from the from tip 36 to the rear tip 80, the smooth, bottom surface 34 is not parallel to the top surface or surfaces of the base 32 at the various portions. For example, the protuberances 48 and 60 are both convex and accordingly their top surfaces 50 and 62, respectively, are curved outwardly, and thus are not parallel to the bottom surface 34. Similarly, the sides of the intermediate portion 52, while comprising a continuation of the sides 42 and 44 of the front portion 33, are not parallel to each other.

The cross sectional configuration of the intermediate portion 52 is of a generally trapezoidal configuration. That is, the intermediate portion 52 includes a top surface 54 which is generally parallel to the bottom surface 34. The intermediate portion 52 also includes a pair of sides which are tapered outwardly and downwardly from the top surface 54 to the bottom surface 34. The top surface 34 accordingly is of a lesser width than the bottom surface 34. A side 56 is shown in FIG. 1, and it tapers outwardly from the top surface 54 to the bottom surface 34. The intermediate portion 52 also includes an opposite side (not shown) comparable to side 56, which also slopes downwardly and outwardly from the top surface 54 to the bottom surface 34. The width of the top surface 54 is relatively narrow between the forward positioning protuberance 48 and the rear positioning protuberance 60. However, the width of the surface 54 increases in the area of the base where the intermediate portion 52 joins the rear portion 58.

At the rear portion 58 there is the rear positioning protuberance 60 which is of a generally convex configuration, as discussed. The cross sectional configuration of the rear section 58 is of a more regular nature, with generally parallel sides. A side 64 is shown in FIG. 1. The convex outer surface 62 of the protuberance is generally of the same width as the bottom surface 34. The width of the rear portion 58 at the rear positioning protuberance 60 is generally the same as the width of the front portion 33 between the tip 36 and the intermediate portion 52, or where the forward positioning protuberance 48 joins to the intermediate portion 52.

Between the rear positioning protuberance 60 and the rear tip 80 on the rear section 58 is a back support 68. The back support 68 includes a slightly convex top surface 70. The back support 68 is wider than the general width of the base 32, and it extends outwardly beyond the base laterally, generally symmetrical with respect to the base 32.

Behind or to the rear of the back support 68 is a belt loop 82. The belt loop 82 extends through the rear portion 58 of the base 32 adjacent to the rear tip 80. The belt 26, shown in phantom in FIG. 2, extends through the belt loop 82, thus securing the user of the prothesis 10 and the support 30 together at two locations, the back of the support 30 as well as the front of the support 30 at the tip 36, as shown in FIG. 2 and 3, and at the base 12 of the prosthesis 10 by way of the notch 24, as discussed above.

In operation, the support 30 is secured by a pin 22 to the bifurcated yoke arms 16 and 18 of the base 12 of the prosthesis 10. The support 30 is then positioned between the legs of the user, with the prosthesis 10 secured to the penis of the user. The upper surface 40 of the front section 33 of the base 32 extends beneath the user's scrotum, with the forward positioning protuberance 48 disposed against the user's torso at the crotch. The user's buttocks will be disposed on either side of the intermediate portion 52, while the rear positioning protuberance 60 contacts the base of the spine of the user. The back support 68 contacts the user's back, also along the lower spine, and at either side of the spine at the lower back, since the back support 68 is of a greater width than is the spine. The support 30 is held against the individual user by means of the strap 26 which extends through the loop 82 to securely hold the support 30 to the user and to the prosthesis 10. The buttocks of the user should tighten as muscles in the buttocks are flexed to hold the buttocks against the sloping sides walls such as side 56, of the intermediate portion 52.

Movement of the user's torso results in a corresponding movement of the prosthesis 10. With a direct connection between the support 30 and the prosthesis 10, a rearward torso movement of the user results in a corresponding movement of the prosthesis 10 as the user's back contacts the rear portion 58 at the positioning protuberance 60 and the back support 70, and a forward movement of the user's torso results in a corresponding movement of the prosthesis 10 through the support 30, as described.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted for specific environments and operative requirements without departing from those principles. The appended claims are intended to cover and embrace any and all such modifications, within the limits only of the true spirit and scope of the invention. This specification and the appended claims have been prepared in accordance with the applicable patent laws and the rules promulgated under the authority thereof.

What is claimed is:

1. Support apparatus for securing a penile prosthesis to a user, comprising in combination:
   base means, including
      a forward portion having a forward tip,
      a forward positioning protuberance for positioning the forward portion against the user's torso,
      an intermediate portion extending rearwardly from the forward portion, and
      a rear portion connected to the intermediate portion and including a rear positioning protuberance; and
   fastening means for securing the base means to the prosthesis.

2. The apparatus of claim 1 in which the fastening means includes means for fastening the forward tip to the prosthesis.

3. The apparatus of claim 2 in which the means for fastening the forward tip to the prosthesis includes a plurality of apertures extending through the base means for securing the base means to the prosthesis at one of several locations to accommodate users of different sizes.

4. The apparatus of claim 3 in which the means for fastening the forward tip to the prosthesis further includes a pin adapted to extend through one of the plurality of apertures to pivotally secure the prosthesis to the forward tip.

5. The apparatus of claim 2 in which the base means further includes a back support on the rear portion adapted to be disposed against a user's back.

6. The apparatus of claim 5 in which the fastening means further includes a belt loop adjacent the back support for receiving a belt to secure the support apparatus to the user.

7. The apparatus of claim 5 in which the base means further includes a rear positioning protuberance on the rear portion between the back support and the intermediate portion.

8. The apparatus of claim 1 in which the base means is curved between the forward tip and the rear portion.

9. The apparatus of claim 1 in which the base means includes a top surface and a bottom surface both extending along the forward, the intermediate, and the rear portions.

10. The apparatus of claim 9 in which the bottom surface of the intermediate portion is wider than the top surface, and the intermediate portion includes a pair of sides extending outwardly from the top surface to the bottom surface.

* * * * *